(12) United States Patent
Sarajlic

(10) Patent No.: US 9,975,761 B2
(45) Date of Patent: May 22, 2018

(54) METHOD OF MANUFACTURING A PLURALITY OF THROUGH-HOLES IN A LAYER OF FIRST MATERIAL

(71) Applicant: SMARTTIP BV, Enschede (NL)

(72) Inventor: Edin Sarajlic, Zutphen (NL)

(73) Assignee: SmartTip BV, Enschede (NL)

( * ) Notice: Subject to any disclaimer, the term of this patent is extended or adjusted under 35 U.S.C. 154(b) by 0 days. days.

(21) Appl. No.: 15/444,086

(22) Filed: Feb. 27, 2017

(65) Prior Publication Data
US 2017/0247252 A1  Aug. 31, 2017

(30) Foreign Application Priority Data

Feb. 25, 2016 (NL) ...................................... 2016328

(51) Int. Cl.
*B81C 1/00* (2006.01)
*A61B 5/15* (2006.01)

(52) U.S. Cl.
CPC ...... *B81C 1/0015* (2013.01); *A61B 5/150396* (2013.01); *B81C 1/00087* (2013.01); *B81C 1/00111* (2013.01); *B81C 1/00119* (2013.01); *B81B 2201/057* (2013.01); *B81B 2201/12* (2013.01); *B81B 2203/0353* (2013.01); *B81C 2201/0132* (2013.01); *B81C 2201/0159* (2013.01); *B81C 2201/0198* (2013.01)

(58) Field of Classification Search
CPC ............... B81C 1/0015; B81C 1/00111; B81C 1/00119
See application file for complete search history.

(56) References Cited

U.S. PATENT DOCUMENTS 6,156,215 A    12/2000   Shimada et al.
7,402,889 B2 *  7/2008   Park .................... H01L 23/5223
                                                         257/532
(Continued)

FOREIGN PATENT DOCUMENTS

WO    2012/098571 A1    7/2012

OTHER PUBLICATIONS

E. Sarajlic et al., Design, Fabrication and Characterization of an In-Plane AFM Probe With Ultra-Sharp Silicon Nitride Tip, Proceedings of the 21st Micromechanics and Micro Systems Eiurope Workshop (MME 2010), Sep. 26, 2010, pp. 24-27, Enschede, Netherlands.

(Continued)

*Primary Examiner* — Mamadou Diallo
(74) *Attorney, Agent, or Firm* — Shewchuk IP Services, LLC; Jeffrey D. Shewchuk

(57) ABSTRACT

A method of manufacturing a plurality of through-holes in a layer of first material, for example for the manufacturing of a probe comprising a tip containing a channel. To manufacture the through-holes in a batch process,

- a layer of first material is deposited on a wafer comprising a plurality of pits
- a second layer is provided on the layer of first material, and the second layer is provided with a plurality of holes at central locations of the pits;
- using the second layer as a shadow mask when depositing a third layer at an angle, covering a part of the first material with said third material at the central locations, and
- etching the exposed parts of the first layer using the third layer as a protective layer.

9 Claims, 8 Drawing Sheets

(56) References Cited

U.S. PATENT DOCUMENTS

| | | | |
|---|---|---|---|
| 2003/0127698 A1* | 7/2003 | Lee | B81B 3/0078 |
| | | | 257/415 |
| 2006/0165957 A1 | 7/2006 | Oesterschulze et al. | |
| 2013/0305519 A1 | 11/2013 | Sarajlic | |
| 2015/0060857 A1* | 3/2015 | Jung | H01L 27/1288 |
| | | | 257/59 |
| 2015/0327371 A1* | 11/2015 | Huang | H05K 3/0035 |
| | | | 264/400 |

OTHER PUBLICATIONS

Berenschot, Erwin J. W. et al., Fabrication of 2D-extruded fractal structures using repeated corner lithography and etching, 9th IEEE Int'l Conf Nano/Micro Engineered and Molecular Systems (NEMS), Apr. 13, 2014, pp. 374-377.

Deladi, S. et al., Fabrication of Micromachined Fountain Pen With in Situ Characterization Possibility of Nanoscale Surface Modification, Journal of Micromechanics & Microengineering, vol. 15, No. 3, Mar. 1, 2005, pp. 528-534, Institute of Physics Publishing, Bristol GB.

* cited by examiner

METHOD OF MANUFACTURING A PLURALITY OF THROUGH-HOLES IN A LAYER OF FIRST MATERIAL

The present invention relates to a method of manufacturing a plurality of through-holes in a layer of first material.

US2006/0165957 discloses a method of method of manufacturing a plurality of through-holes in a layer of material wherein an intermediate product is subjected to a plurality of method steps, the intermediate product
  defining a first side and a second side, and
  comprises a base substrate, said base substrate comprising a base material, wherein at the first side the surface of the base substrate defines a main plane;
  wherein the plurality of method steps comprises the steps of
  providing the base substrate of the intermediate product at the first side with a plurality of pits in said base material,
  providing the base substrate with the layer of first material at the first side of the intermediate product, the first material being different from the base material so as to result in the intermediate product having pits comprising a layer of said first material,
  providing a plurality of holes in the layer of first material at the central locations of the pits, and
  subjecting the intermediate product to directional dry etching to provide holes in the base substrate.

Through-holes are provided by etching from the second side.

Various MEMS devices, such as i) probes comprising a hollow cantilever or ii) sieves, comprise at least one through-hole in a layer of first material such as silicon nitride. The through-hole is for example in a face of a pyramidal tip of the cantilever of a MEMS probe. MEMS probes comprising hollow cantilevers having a tip are used in life sciences for a variety of purposes, two of them being the delivery of a substance to or extraction of material from a cell. In that case, the tip of the MEMS probe will have to penetrate through the cell wall. Material of the cell wall should not clog the opening at the tip of the probe. For this reason, preference is given to probes having the opening (through-hole) in a side wall or pyramidal edge of the tip, instead of at the tip's distal end. In the art, probes with a cantilever comprising a conduit and having a tip are routinely produced. To create the opening of the conduit at the tip, use is made of ion beam etching, wherein a beam of ions is focussed on a wall of a tip to locally etch said wall of first material and form the through-hole.

While MEMS techniques allow MEMS devices such as probes comprising cantilevers having a tip to be manufactured in large numbers simultaneously, this step of creating the opening (a through-hole) at the tip, has to be performed for each tip individually and consecutively by focussed ion beam milling, which is time consuming and costly. Also, there is a risk of damage to the opposite wall of the tip once the focussed beam has penetrated the wall of the tip.

The objective of the present invention is to provide a method allowing for the creation of through-holes in a batch process, i.e.
  simultaneously creating a multitude of through-holes. It is a further object of the present invention to provide a method allowing for the batch-wise production of through-holes in pits comprising a layer of the first material, the through-holes being at a distance from the distal ends of said tips.

To this end, a method according to the preamble is characterized in that an intermediate product is subjected to a plurality of method steps, the intermediate product
  defining a first side and a second side, and
  comprises a base substrate, said base substrate comprising a base material, wherein at the first side the surface of the base substrate defines a main plane;
  wherein the plurality of method steps comprises the steps of
  providing the intermediate product as a base substrate, said base substrate comprising a base material, wherein at the first side the surface of the base substrate defines a main plane;
  providing the base substrate of the intermediate product at the first side with a plurality of pits in said base material, and
  providing the base substrate with a layer of first material at the first side of the intermediate product, the first material being different from the base material so as to result in the intermediate product having pits comprising a layer of said first material,
  providing a second layer of a second material different from the first material on the layer of first material, and
  providing the second layer of the second material with a plurality of holes, the holes being provided at central locations of the pits;
  depositing a third layer of a third material different from the first material on the second layer of the second material, said depositing being performed at an angle a to the normal to the base main plane of at least 5° using said second layer of second material as a shadow mask, covering a part of the first material of the first layer with said third material at the central locations, and
  etching the exposed parts of the layer of said first material using the third layer of third material as a protective layer to provide through-holes in the layer of first material.

Thus, the layer of first material is exposed at off-center areas of the central locations and subjected to etching at a plurality of exposed off-center locations simultaneously, as a result of which holes are formed in said layer of first material. Subsequent removal of base material at the location of the pits will result in a plurality of through-holes accessible from both the first side and the second side.

In the present application, the base substrate will in general be a wafer. The wafer is for example a silicon wafer, which may be used to manufacture probes comprising four-sided or three-sided pyramidal pits, as desired, depending on the crystal orientation of the starting wafer with respect to the base main plane. For four-sided and three-sided pyramidal tips these are 100 and 111 silicon respectively.

The method according to the invention is less sensitive to the processing conditions of the step of directional dry etching, because over etching merely results in damage to the base material of the substrate, which for many applications will be removed anyway.

After locally penetrating the layer of first material, the method will be continued using any conventional steps for manufacturing the MEMS device that is desired. By way of example, for a probe comprising a hollow conduit, a sacrificial conduit layer will be provided, followed by further wall material for the conduit covering said sacrificial conduit layer, and etching to remove the sacrificial conduit layer material, so as to result in a hollow conduit. Removing crystalline base material at the location of the pyramidal pit will result in a freely extending cantilever. Such methods are known in the art, for example from WO2012/096571.

The angle α will in general be less than 45°, such as less than 35°.

The step of etching may be performed using wet etching, although for improved process control dry etching will in general be preferred.

The second material of the second layer and the third material of the third layer may be the same, e.g. a metal such as chromium.

According to a favourable embodiment, removing base material of the base substrate exposing the through-holes in the second layer of material.

It is preferred to remove the base material after creating the through-holes in the second layer, instead of before.

According to a favourable embodiment, the step of etching comprises directional dry etching, preferably Reactive Ion Etching (RIE).

This allows to further control the formation of the through-hole.

According to a favourable embodiment, the method further comprises after the step of etching part of the layer of first material using the third layer of third material as a protective layer a step of removing the second layer and third layer.

Thus after serving their purpose these helper layers are removed.

According to a favourable embodiment, the method comprises at least one further method step for manufacturing a plurality of MEMS devices, a MEMS device comprising a through-hole in the layer of first material formed by the step of etching part of the layer of said first material.

A typical MEMS device according to the present invention is a probe, e.g. for taking a sample from a cell, or introducing material into a cell.

According to a favourable embodiment, the method comprises further steps for manufacturing a plurality of probes wherein
    each probe of the plurality of probes comprises
        a probe base section
            having a probe base main plane, and
            comprising a first opening of a conduit; and
        a cantilever protruding from said probe base section parallel with the probe base main plane, said cantilever having
            a proximal end connected to the probe base section, and
            a distal cantilever end;
        said cantilever comprising a tip having a distal tip end, said tip comprising a second opening of said conduit at a location away from the distal tip end;
wherein the second opening is formed by at least one step comprising the step of etching part of the layer of said first material using the third layer of third material as a protective layer.

MEMS probes are an important application area and for the state of the art forming the second opening in a face of the tip, i.e. not at the terminal point of the tip, is a major cost factor because so far they had to be milled individually with accurate aiming of a focussed ion beam. The present invention does not require ion beam milling individual tips. The term "in a face" does not exclude that the hole is in two adjacent faces, i.e. crossing a pyramidal ridge.

According to a favourable embodiment, the probe comprises a hollow cantilever.

This is an important application area of the method according to the invention.

According to a favourable embodiment, the base material is a crystalline base material, and before the base substrate is provided with the layer of first material, the method comprises the step of
    etching the base substrate at the first side to form a plurality of pits in said crystalline base material, the pits comprising a face that is at an angle to the main plane.

Pits are typically formed using anisotropic etching of the base material, which allows for the formation of pyramidal pits. Thus MEMS techniques allow for the manufacture of probes having a sharp pyramidal tip. With a probe comprising a sharp tip, excessive damage to the cell is to be avoided. The probe may also serve a dual role, because the tip may be used for scanning using one of a variety of scanning techniques known in the art. A typical crystalline base material used in the art is silicon (1,0,0).

The face will extend along a crystal plane of the base material.

Phrased in the two-part form, the invention relates to a method of manufacturing a plurality of through-holes in a layer of first material wherein an intermediate product is subjected to a plurality of method steps, the intermediate product
    defining a first side and a second side, and
    comprises a base substrate, said base substrate comprising a base material, wherein at the first side the surface of the base substrate defines a main plane;
    wherein the plurality of method steps comprises the steps of
    providing the intermediate product as a base substrate, said base substrate comprising a base material, wherein at the first side the surface of the base substrate defines a main plane;
    providing the base substrate of the intermediate product at the first side with a plurality of pits in said base material, and
    providing the base substrate with a layer of first material at the first side of the intermediate product, the first material being different from the base material so as to result in the intermediate product having pits comprising a layer of said first material, and
    etching part of the layer of said first material to provide through-holes in the layer of first material;
    characterized in that the method further comprises
    after the step of providing the layer of first material and before the step of etching
    providing a second layer of a second material different from the first material on the layer of first material, and
    providing the second layer of the second material with a plurality of holes, the holes being provided at central locations of the pits;
    depositing a third layer of a third material different from the first material on the second layer of the second material, said depositing being performed at an angle a to the normal to the base. In conjunction with this, it relates to all the appended subclaims as well.

The present invention will now be illustrated with reference to the drawing where FIG. 1 shows a probe as can be manufactured using the method according to the invention, in top view (top) and cross-sectional view (bottom), both views being vertically aligned;

Figure 1:
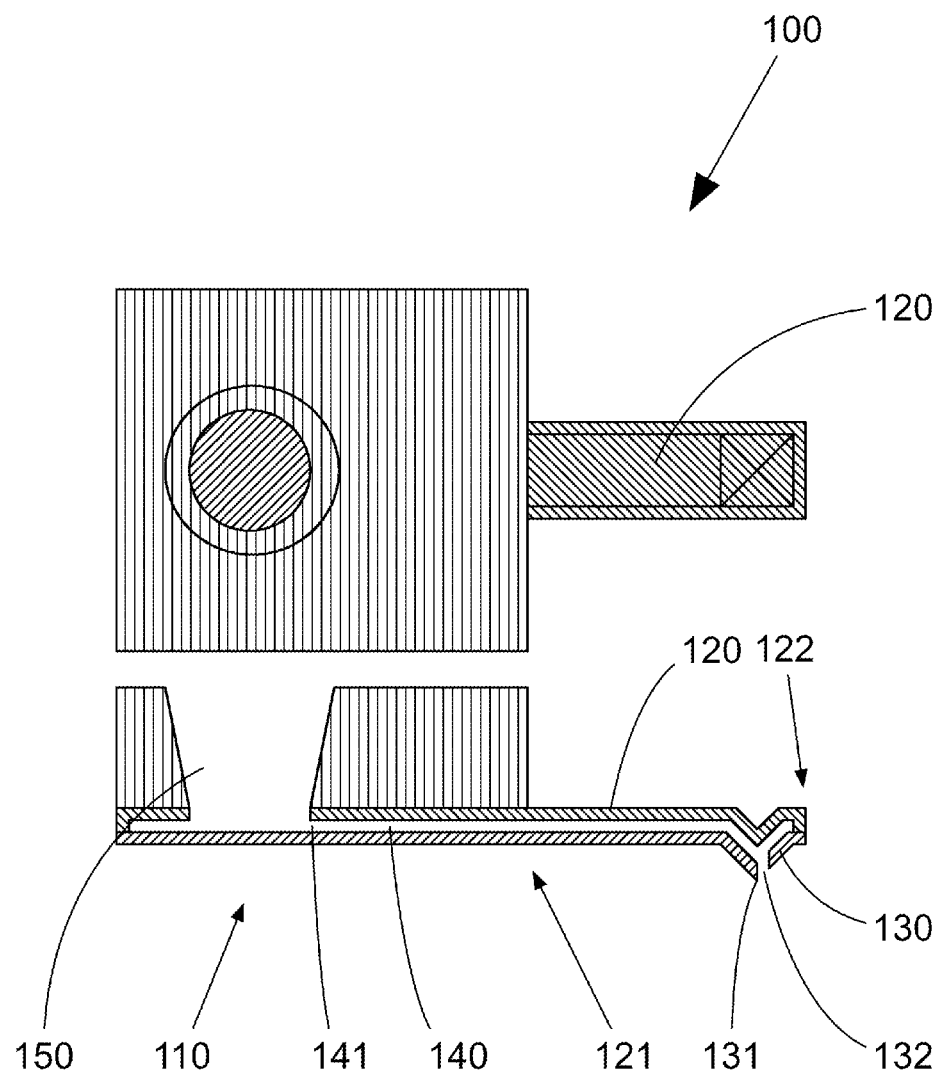
FIG. 1 shows a probe 100 as can be manufactured using the method according to the invention, in top view (top) and cross-sectional view (bottom), both views being vertically aligned.

The probe 100 comprises a probe base section 110 and a cantilever 120 extending from the probe base section 110. The cantilever 120 has a proximal end 121 connected to the probe base section 110 and a distal cantilever end 122.

The distal cantilever end 122 comprises a pyramidal tip 130 comprising a pyramidal tip end 131. In a face of the pyramidal tip 130, i.e. away from the pyramidal tip end 131, there is a through-hole 132 manufactured in accordance with the present invention.

The probe 100 comprises an elongated conduit 140 extending from a reservoir 150 at the probe base section 110 through the cantilever 120 to the through-hole 132.

The conduit 140 comprises a first opening 141 and the second opening is defined by the through-hole 132.

The method according to the invention will now be illustrated using FIG. 2A to FIG. 2J, which show in top view and cross-sectional view a method of manufacturing the probe 100 of FIG. 1. The method according to the present invention allows for a multitude of through-holes 132 and hence probes 100 to be manufactured at once, but the figures will show one probe 100 in the making only.

A silicon wafer 200 having a thickness of 380 um is shown (FIG. 2A) in top view. The silicon wafer 200 used as base substrate 200 is of (1,0,0) silicon. If a pyramidal tip with three faces is desired, (1,1,1) silicon may be used instead.

The top surface of the silicon wafer defines a main base plane.

Figure 2A:
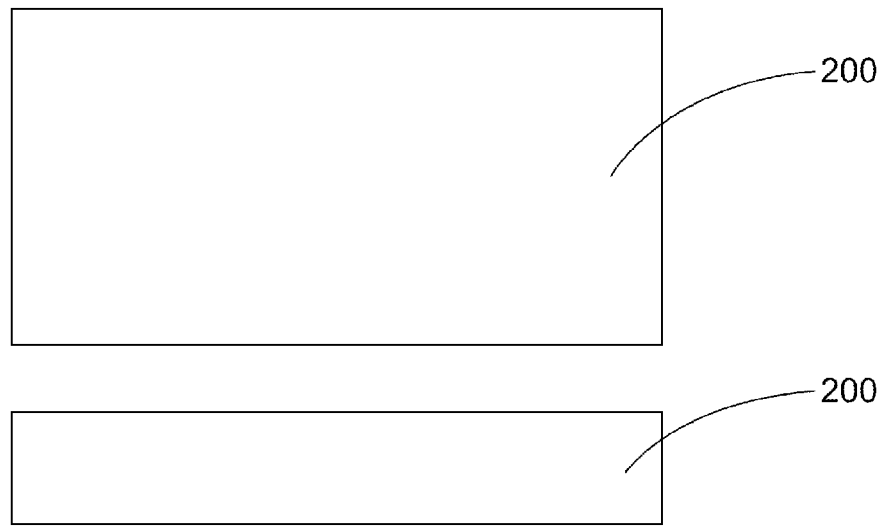
FIG. 2A to FIG. 2J illustrate a method of manufacturing the probe according to FIG. 1 in top view (top) and cross-sectional view (bottom), both views being vertically aligned.
Figure 2B:
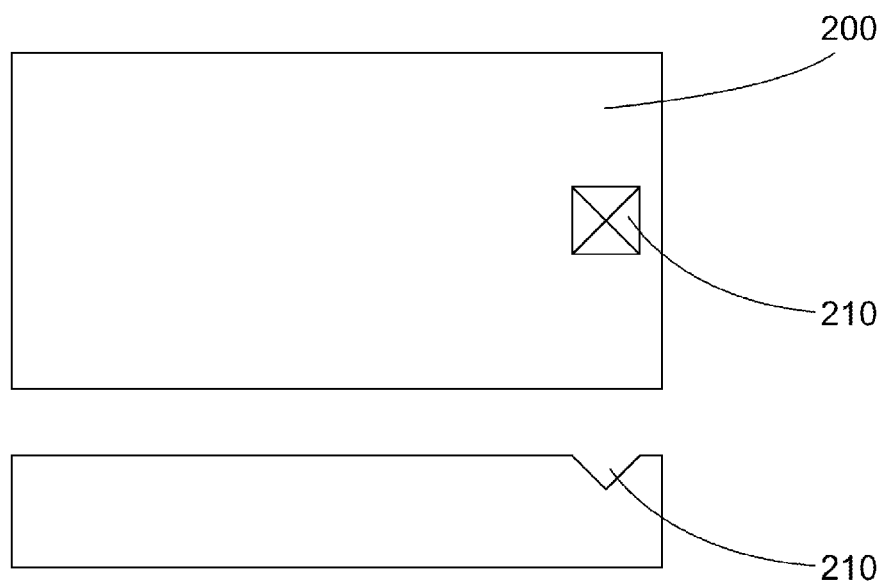

Using a mask, pyramidal pits 210 (only one shown, singulars are used in the remainder of the figure description) is etched by wet anisotropic etching of the silicon using 25% KOH (FIG. 2B). The pyramidal pit 210 is 10 um×10 um.

Figure 2C:
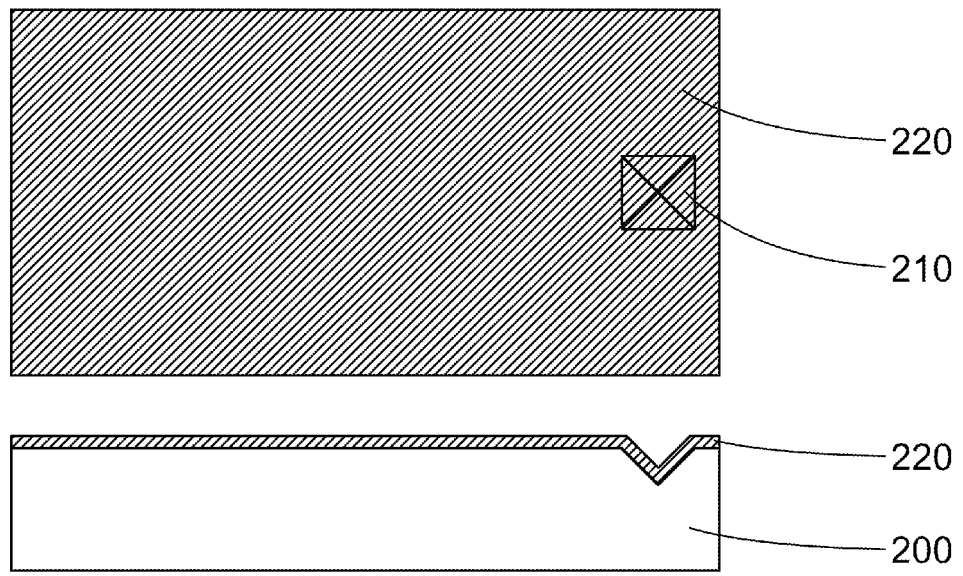

A thin layer of first material 220 (350 nm), here silicon nitride, is deposited (FIG. 2C) on the silicon wafer 200 comprising a pyramidal pit 210 (FIG. 2C). The silicon nitride will be part of a wall defining the conduit 140 and the pyramidal tip 130.

Figure 2D:
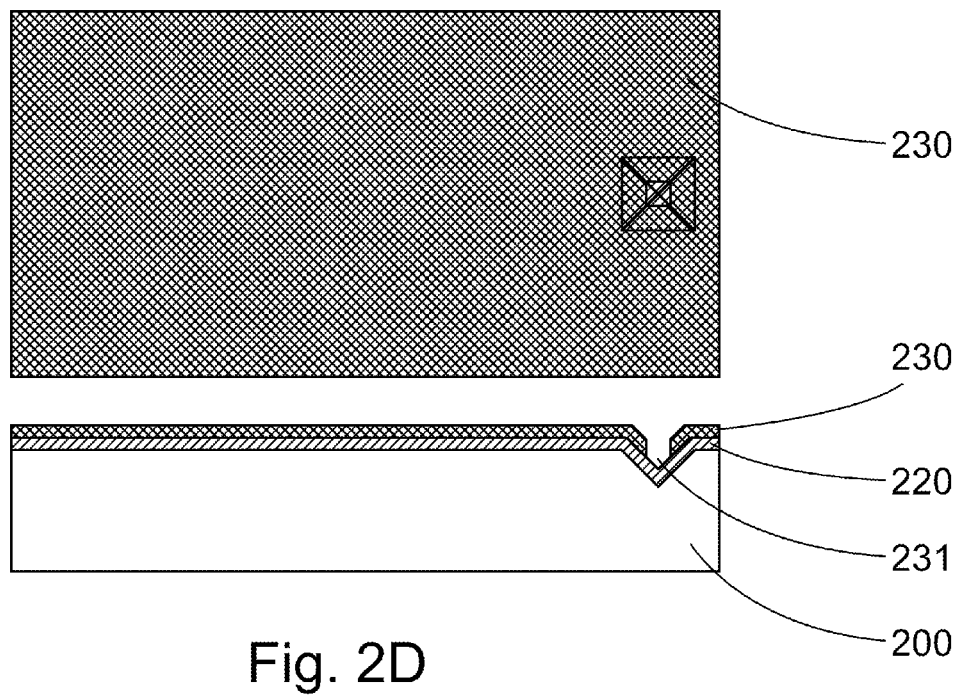
Figure 2E:
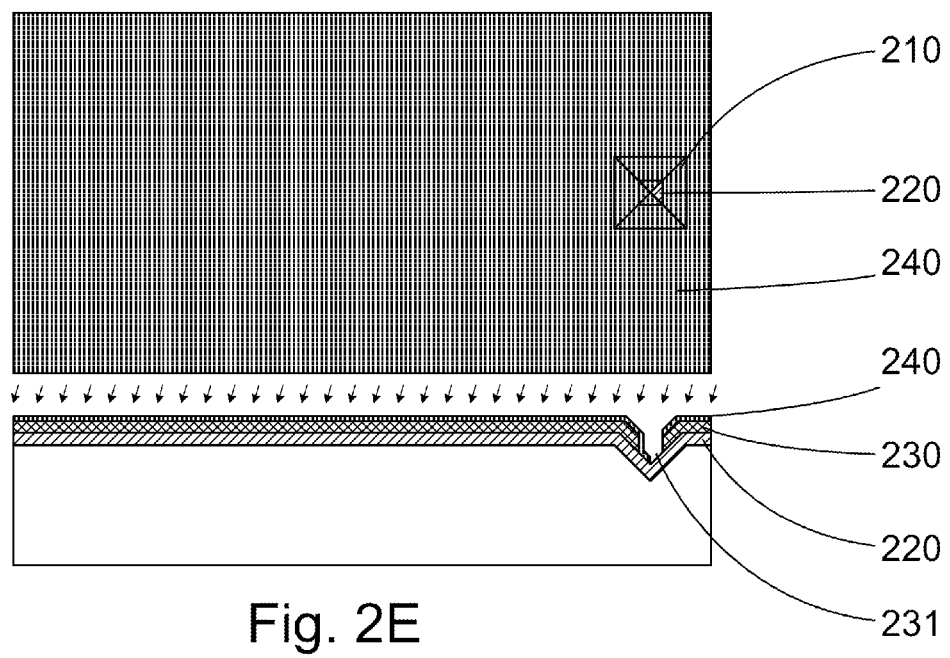

A thin layer of a second material 230 in this case 400 nm thick silicon oxide was formed as a shadow mask material on top of the first layer of first material 220 and provided with a small opening 231 centrally located at the bottom of the pyramidal pit 210 using corner lithography (FIG. 2D).

Other techniques can be used instead, for example deposition of silicon oxide by Low Pressure or Plasma Enhanced Chemical Vapor Deposition (LPCVD or PECVD) followed by optical lithography and silicon oxide etching.

The central location of a pit is the location where the pit is the deepest. Typically the central openings 231 are concentric holes.

The wafer 200 provided with the second layer of second material 230 (silicon dioxide; 200 um) is provided with a protective third layer of a third material 240 (chromium) using a directional depositing technique. We used evaporation at an angle a to the normal to the main base plane of 25°. The second layer of second material 230 and the angle of the pit 210 (35.26° relative to the line normal to the surface of the main base plane) cooperate and the second layer of second material 230 acts as a shadow mask, as a result of which chromium is deposited only on an off-center part of the first layer of first material 220 exposed by the opening 231. The thickness of the third layer of third material 240 was 80 um.

With the third metal layer of third material 240 in place, the wafer is subjected to etching, such as wet etching. In this case, Reactive Ion Etching (RIE) was performed, exposing the third layer of third material as a layer protecting against the RIE, and exposing and etching the first layer of first material 220 where chromium was not deposited due to the shadow mask effect of the second layer of the second material 230. RIE was performed as usual, i.e. perpendicular to the main base plane.

Figure 2F:
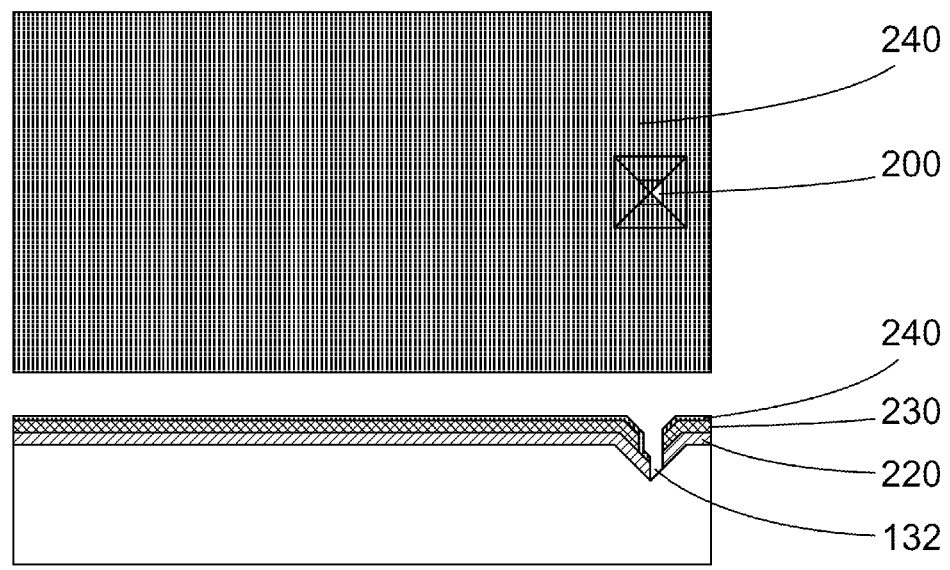

This results in through-hole 132 (FIG. 2F). Because a plurality of probes is manufactured using the present method, a plurality of through-holes 132 is formed at the same time, and not formed consecutively. The position of the through-hole 132 can to some extent be tuned by adjusting the angle a at which the protective third layer of third material is deposited and/or in case of directional etching such as RIE on the angle of directional etching.

Figure 2G:
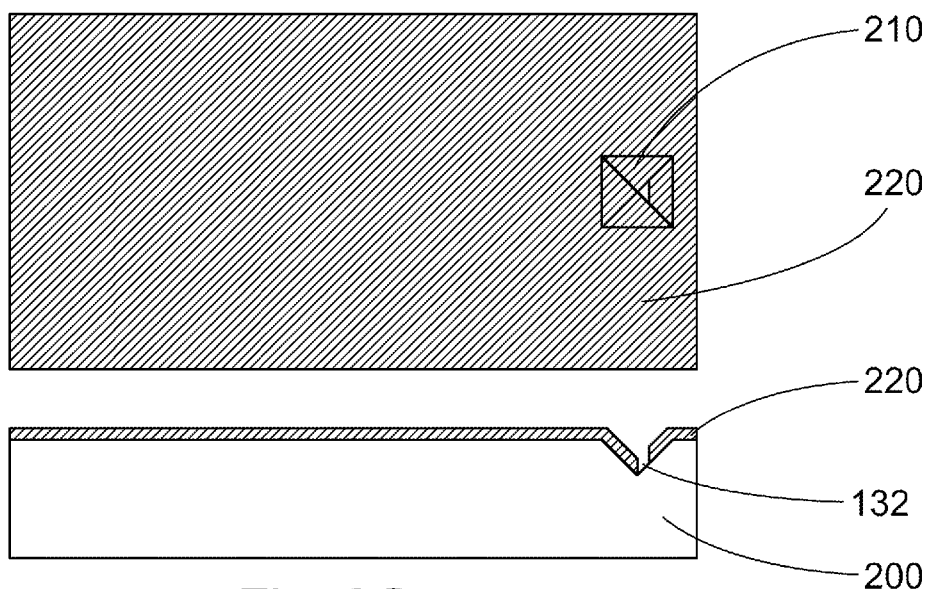

Now the silicon dioxide layer of material 230 and the metalic third layer 240, i.e. the layers that served as a masking material, are removed using commericially available chromium etchant and using hydrofluoric acid in accordance with standard practice (FIG. 2G).

Figure 2H:
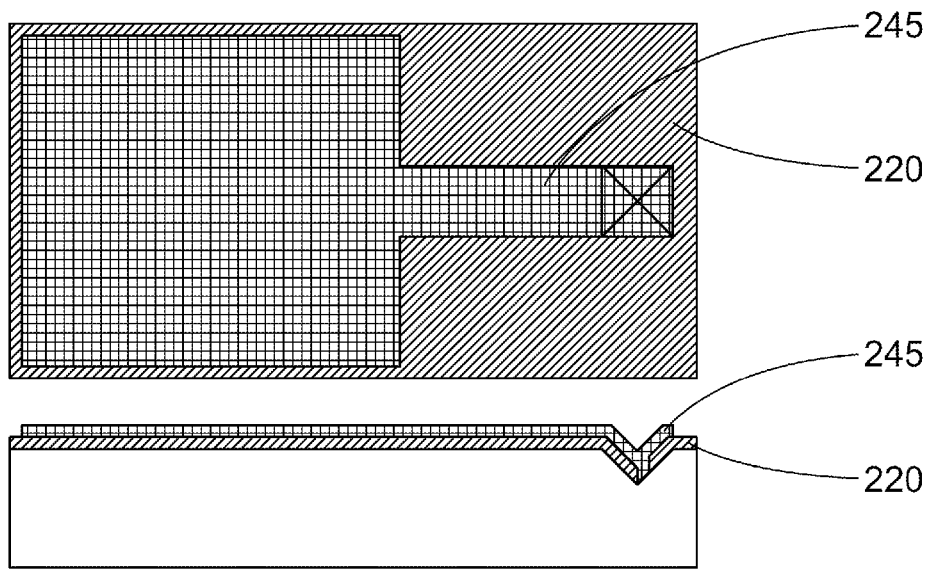
Figure 2I:
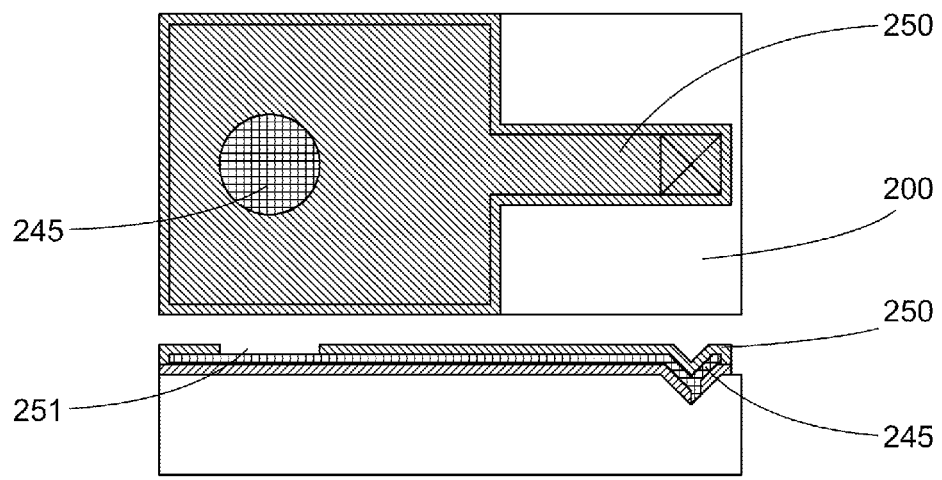

The remainder of the probe 100 is manufactured according to well-known practices, by providing the wafer obtained in the previous step with a patterned layer of sacrificial material 245, here polycrystalline silicon with a thickness of 1 um (FIG. 2H).

A further layer 250 of silicon nitride having a thickness of 350 nm is deposited, covering the silicon nitride layer of material 220 and the layer of sacrificial material 245. It is subsequently etched by RIE (Reactive Ion Etching) to create an etching window 251 so as to expose part of the sacrificial layer of material 245 at a location that will later on be at the probe base section 110.

Figure 2J:
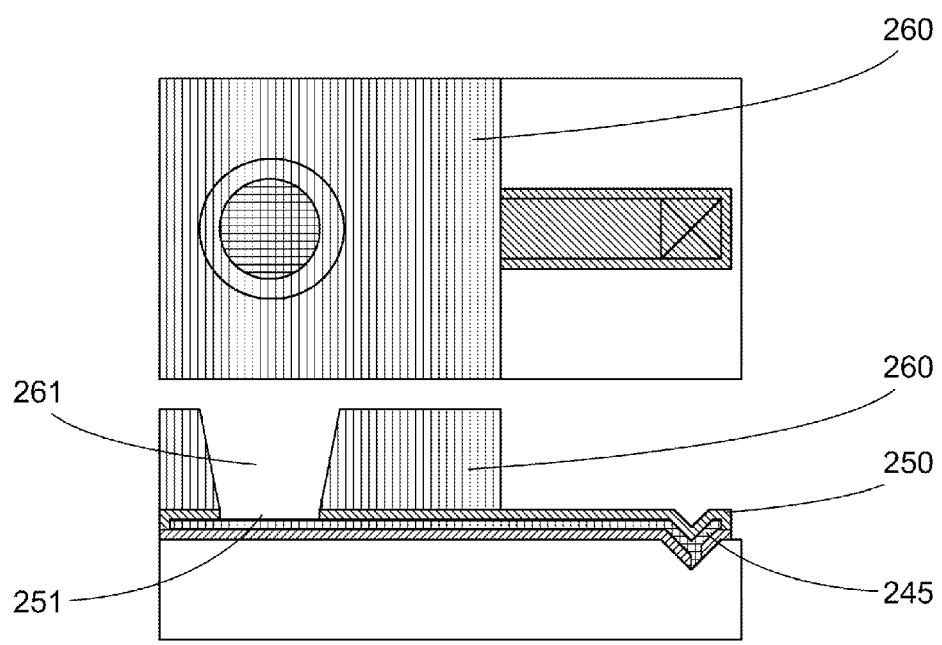

The further layer of material 250 is bonded to a glass cover 260 by anodic bonding (FIG. 2J). The glass cover 260 has a cover hole 261 (a through-hole) that will allow access of etchant to the polycrystalline sacrificial material at the location of the cover hole 261 and, once the silicon of the wafer has been etched away, at the through-hole 132.

Etching with Tetramethylammonium hydroxide (TMAH) results in the probe 100, shown in FIG. 1.

Figure 3A:
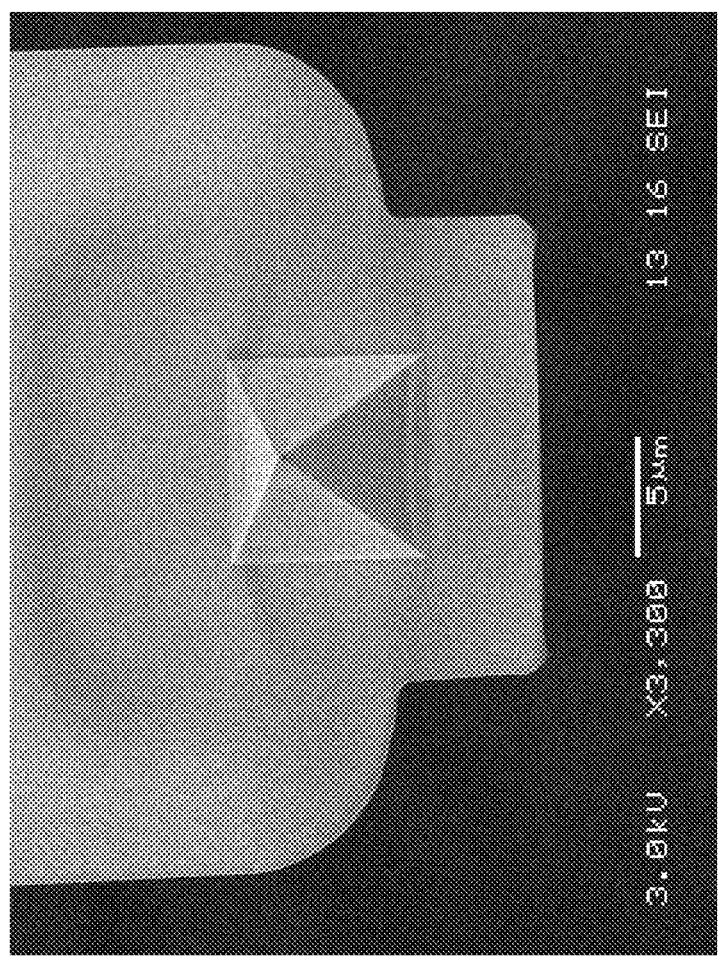
FIG. 3a shows a Scanning Electron Microscope image of a probe manufactured according to the invention.

FIG. 3A shows a Scanning Electron Microscope image of a probe 100 manufactured according to the invention. The pyramidal tip 130 and part of cantilever 120 are visible. The through-hole 132 is near the very end of the pyramidal tip.

Figure 3B:
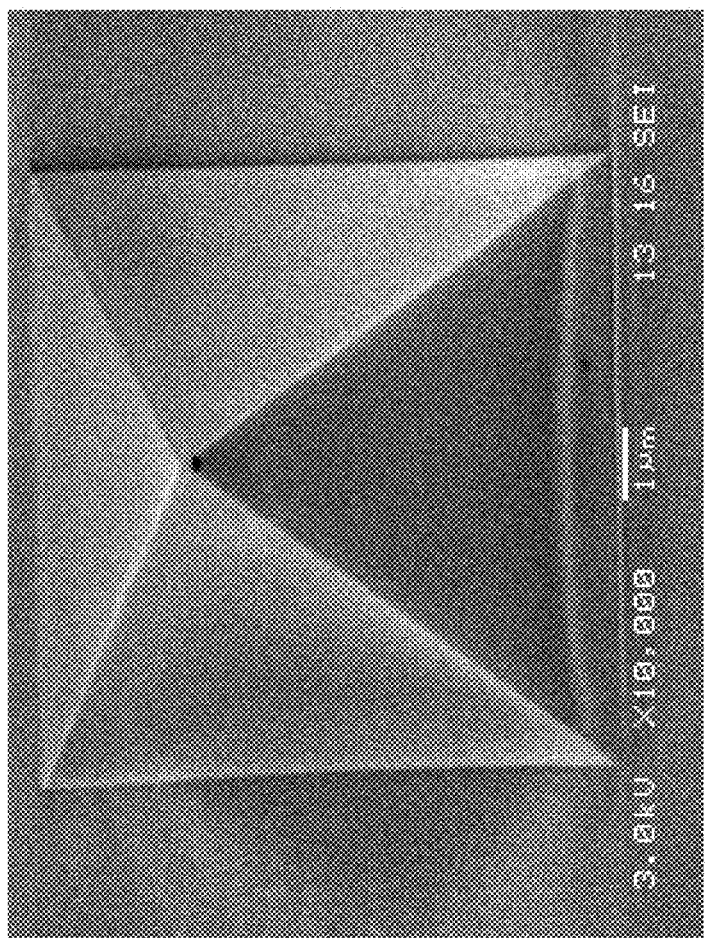
FIG. 3b shows a detail of the probe of FIG. 3A.

FIG. 3B shows a zoomed in SEM picture, showing a detail of the probe 100 of FIG. 3A. The through-hole 132 is visible near the tip end 131 of the pyramidal tip 130.

The invention claimed is:

1. A method of manufacturing a plurality of through-holes in a layer of first material;
   wherein an intermediate product is subjected to a plurality of method steps, the intermediate product
      defining a first side and a second side, and
      comprises a base substrate, said base substrate comprising a base material, wherein at the first side the surface of the base substrate defines a main plane;
   wherein the plurality of method steps comprises the steps of
      providing the intermediate product as a base substrate, said base substrate comprising a base material, wherein at the first side the surface of the base substrate defines a main plane;
      providing the base substrate of the intermediate product at the first side with a plurality of pits in said base material, and providing the base substrate with a layer of first material at the first side of the intermediate product, the first material being different from the base material so as to result in the intermediate product having pits comprising a layer of said first material, providing a second layer of a second material different from the first material on the layer of first material, and providing the second layer of the second material with a plurality of holes, the holes being provided at central locations of the pits;

depositing a third layer of a third material different from the first material on the second layer of the second material, said depositing being performed at an angle a to the normal to the base main plane of at least 5° using said second layer of second material as a shadow mask, covering a part of the first material of the first layer with said third material at the central locations, and etching the exposed parts of the layer of said first material using the third layer of third material as a protective layer to provide through-holes in the layer of first material.

2. The method according to claim 1, wherein removing base material of the base substrate exposes the through-holes.

3. The method according to claim 1, wherein the step of etching comprises directional dry etching.

4. The method according to claim 1, wherein the method further comprises after the step of etching part of the layer of first material using the third layer of third material as a protective layer a step of removing the second layer and third layer.

5. The method according to claim 1, wherein the method comprises at least one further method step for manufacturing a plurality of MEMS devices, a MEMS device comprising a through-hole in the layer of first material formed by the step of etching part of the layer of said first material.

6. The method according to claim 5, wherein the method comprises further steps for manufacturing a plurality of probes wherein each probe of the plurality of probes comprises
a probe base section
having a probe base main plane, and
comprising a first opening of a conduit; and
a cantilever protruding from said probe base section parallel with the probe base main plane, said cantilever having
a proximal end connected to the probe base section, and
a distal cantilever end;
said cantilever comprising a tip having a distal tip end, said tip comprising a second opening of said conduit at a location away from the distal tip end;
wherein the second opening is formed by at least one step comprising the step of etching part of the layer of said first material using the third layer of third material as a protective layer.

7. The method according to claim 1, wherein the probe comprises a hollow cantilever.

8. The method according to claim 1, wherein the base material is a crystalline base material, and before the base substrate is provided with the layer of first material, the method comprises the step of etching the base substrate at the first side to form a plurality of pits in said crystalline base material, the pits comprising a face that is at an angle to the main plane.

9. The method according to claim 3, wherein the step of etching comprises Reactive Ion Etching (RIE).

* * * * *